(12) United States Patent
Stanfield et al.

(10) Patent No.: US 12,377,257 B2
(45) Date of Patent: *Aug. 5, 2025

(54) HEART ASSIST DEVICE

(71) Applicant: STAR BP, INC., Spring, TX (US)

(72) Inventors: J. Ryan Stanfield, Sandy, UT (US); Michael Vladovich, Edmond, OK (US); Timothy R. Maher, Hamilton, MO (US)

(73) Assignee: STAR BP, INC., Spring, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/775,778

(22) Filed: Jul. 17, 2024

(65) Prior Publication Data

US 2024/0366927 A1    Nov. 7, 2024

Related U.S. Application Data

(60) Division of application No. 18/341,734, filed on Jun. 26, 2023, now Pat. No. 12,076,546, which is a
(Continued)

(51) Int. Cl.
| | |
|---|---|
| *A61M 60/148* | (2021.01) |
| *A61M 60/178* | (2021.01) |
| *A61M 60/216* | (2021.01) |
| *A61M 60/416* | (2021.01) |
| *A61M 60/419* | (2021.01) |

(Continued)

(52) U.S. Cl.
CPC ........ *A61M 60/148* (2021.01); *A61M 60/178* (2021.01); *A61M 60/216* (2021.01); *A61M 60/416* (2021.01); *A61M 60/419* (2021.01); *A61M 60/422* (2021.01); *A61M 60/585* (2021.01); *A61M 60/824* (2021.01); *A61M 60/857* (2021.01); *A61M 60/873* (2021.01); *A61M 60/876* (2021.01); *A61M 60/88* (2021.01)

(58) Field of Classification Search
None
See application file for complete search history.

(56) References Cited

U.S. PATENT DOCUMENTS

| | | | |
|---|---|---|---|
| 8,409,276 B2* | 4/2013 | Wampler | A61M 60/831 623/3.13 |
| 8,731,664 B2* | 5/2014 | Foster | A61M 60/165 607/16 |

(Continued)

*Primary Examiner* — Juan G Flores
(74) *Attorney, Agent, or Firm* — Ewing & Jones, PLLC

(57) ABSTRACT

A rotary pump housing having a cylindrical bore, a pumping chamber and a motor stator including an electrically conductive coil located within the housing and surrounding a portion of the cylindrical bore. A rotor has a cylindrical shaft with an impeller and one or more magnets located within the shaft that are responsive to the motor stator to drive actuation of the rotor. The housing bore is closely fitted to the outer surface of the shaft forming a hydrodynamic journal bearing with an annular clearance defining a leakage flow path. One or more of radial or axial thrust bearings may be provided to provide rotation stability to the rotor and flow within the leakage flow path. The relative orientation of positions of the inflow, outflow, and leakage flow paths may be varied within the pump, such as to accommodate different intended methods for implantation and/or use.

6 Claims, 6 Drawing Sheets

Related U.S. Application Data continuation of application No. 16/920,720, filed on Jul. 5, 2020, now Pat. No. 11,724,093, which is a continuation of application No. PCT/US2018/012736, filed on Jan. 8, 2018.

(51) Int. Cl.
*A61M 60/422* (2021.01)
*A61M 60/585* (2021.01)
*A61M 60/824* (2021.01)
*A61M 60/857* (2021.01)
*A61M 60/873* (2021.01)
*A61M 60/876* (2021.01)
*A61M 60/88* (2021.01)

(56) References Cited

U.S. PATENT DOCUMENTS

| | | | |
|---|---|---|---|
| 11,724,093 B2 * | 8/2023 | Stanfield | A61M 60/419 600/16 |
| 2009/0149950 A1 * | 6/2009 | Wampler | A61M 60/178 623/3.13 |
| 2010/0174131 A1 * | 7/2010 | Foster | A61M 60/824 600/16 |

* cited by examiner

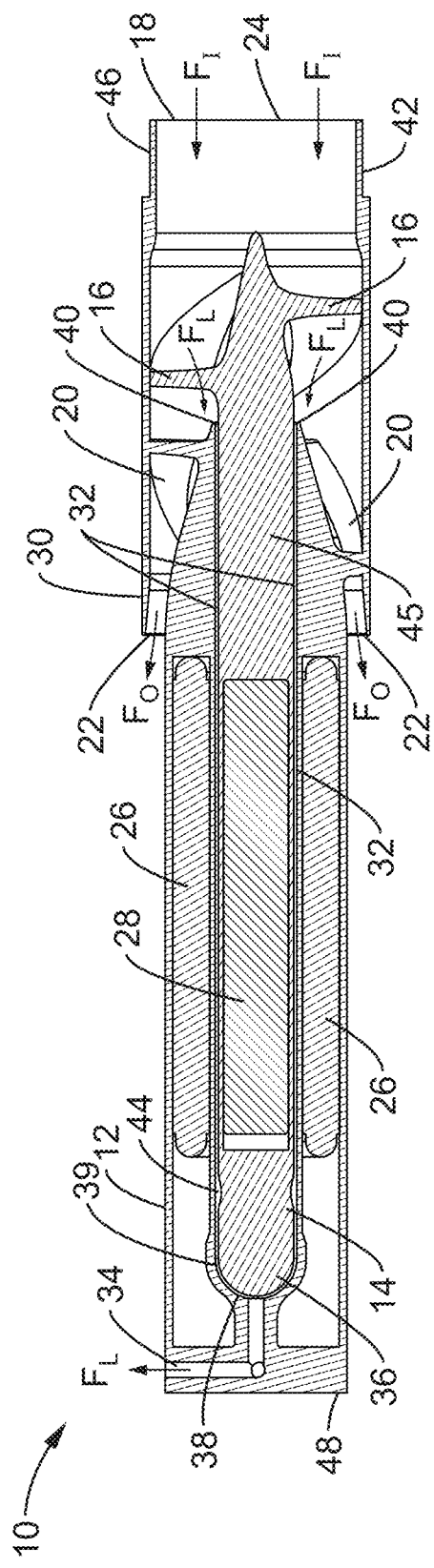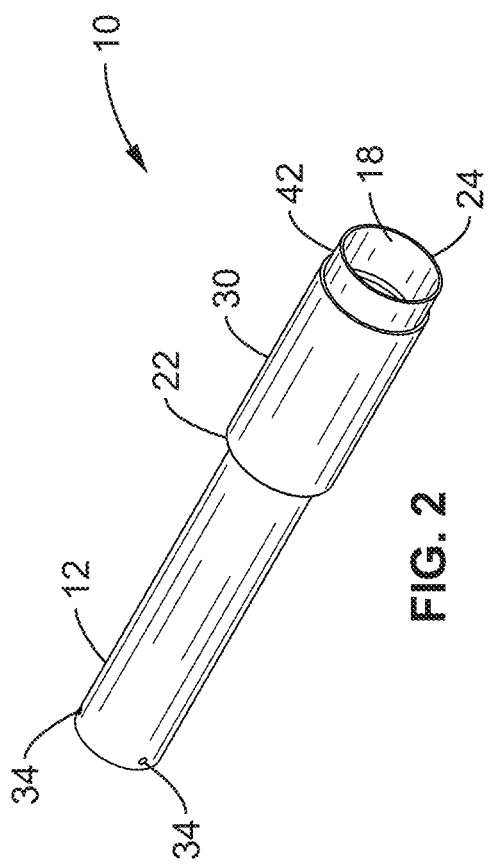
FIG. 1
FIG. 2

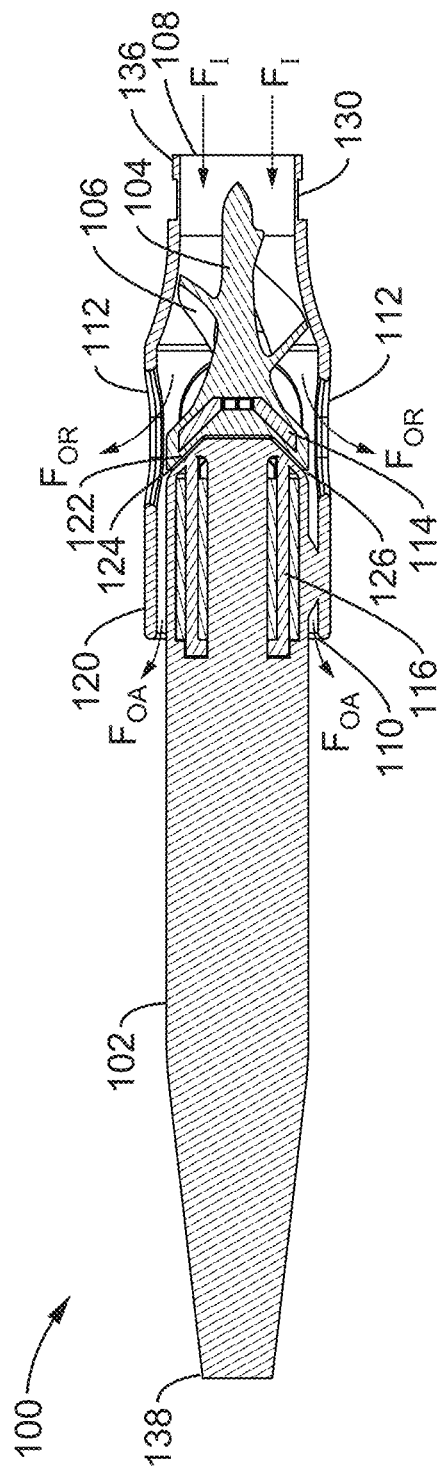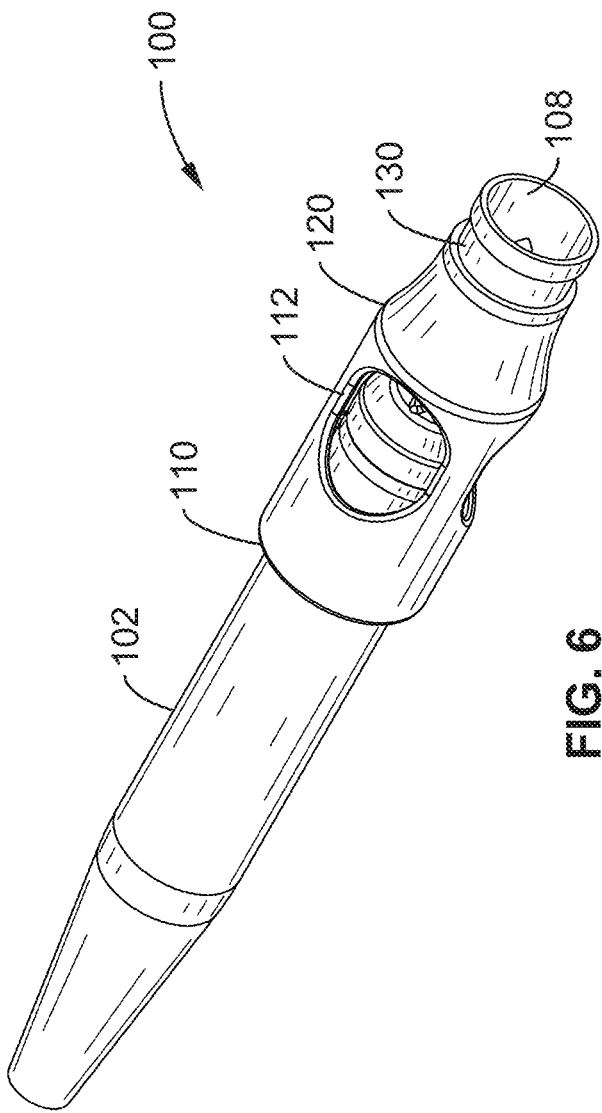
FIG. 5
FIG. 6

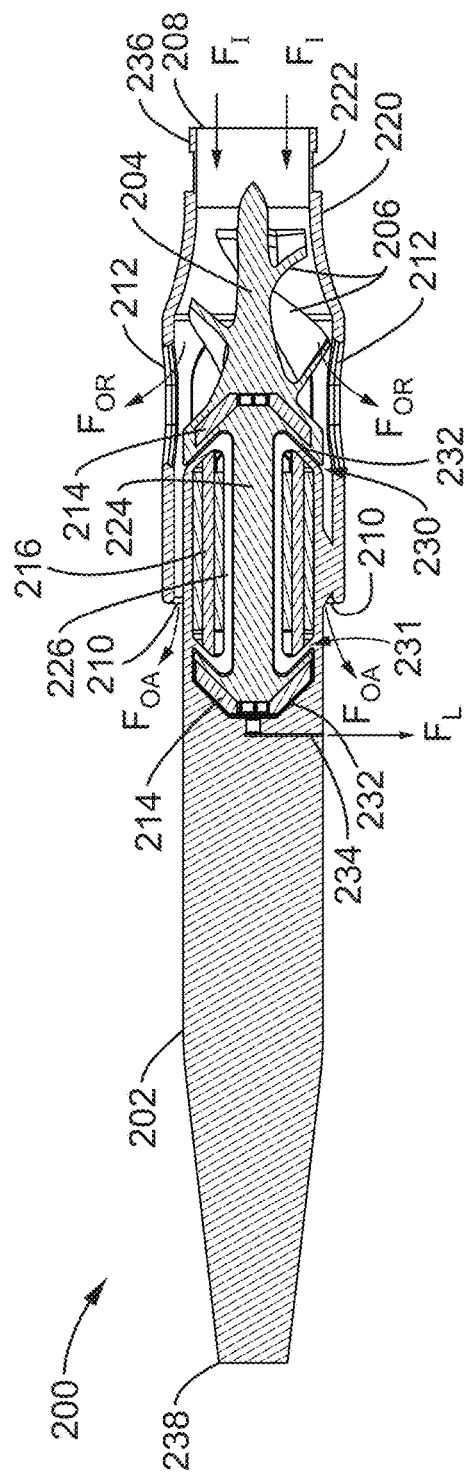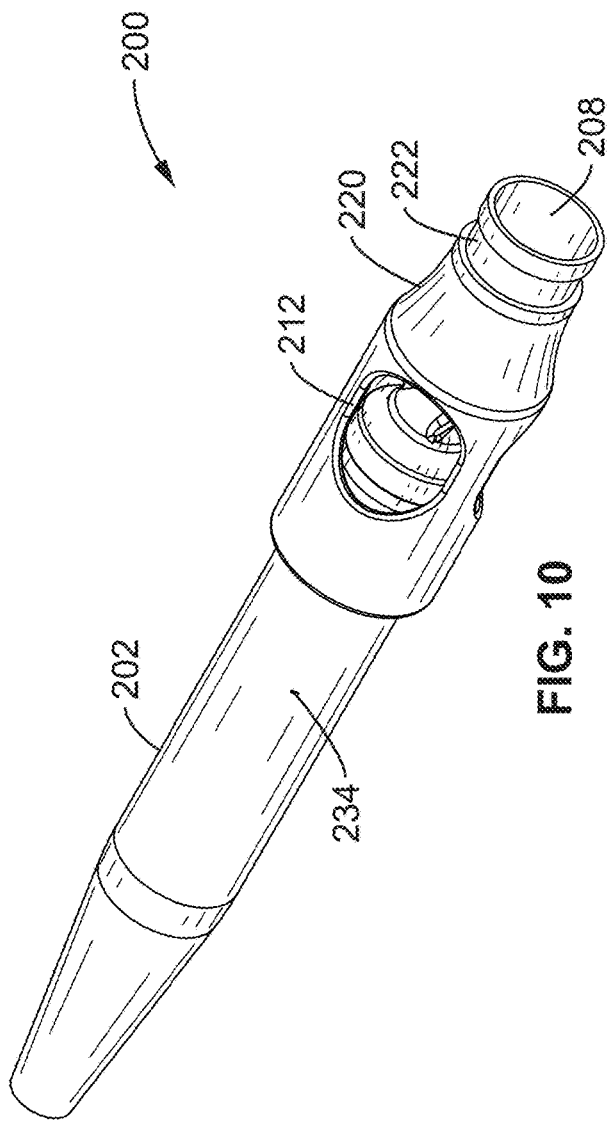
FIG. 9
FIG. 10

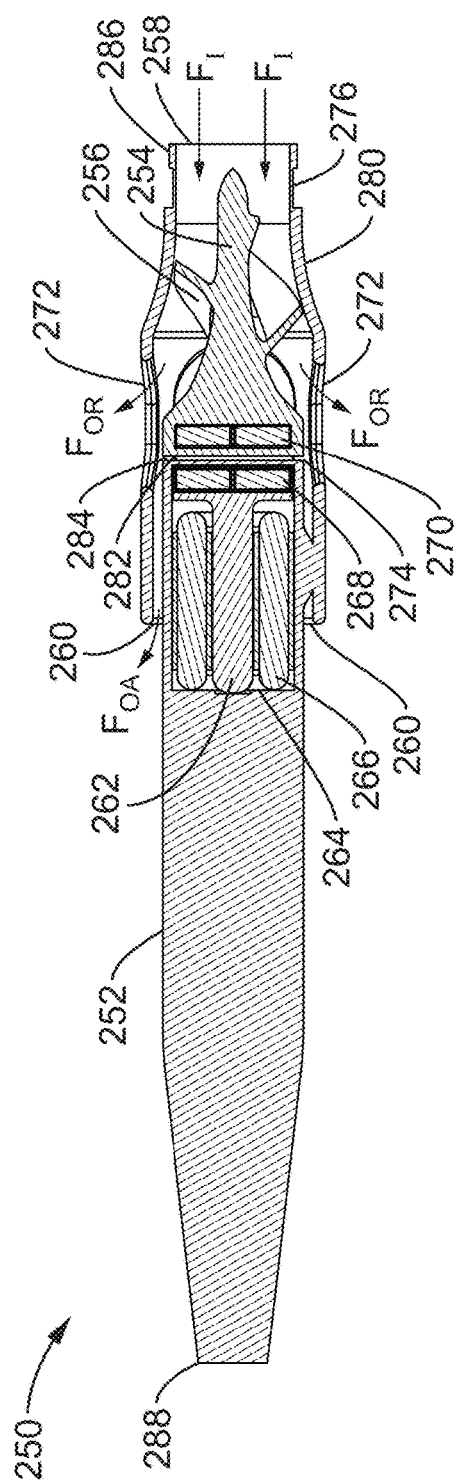
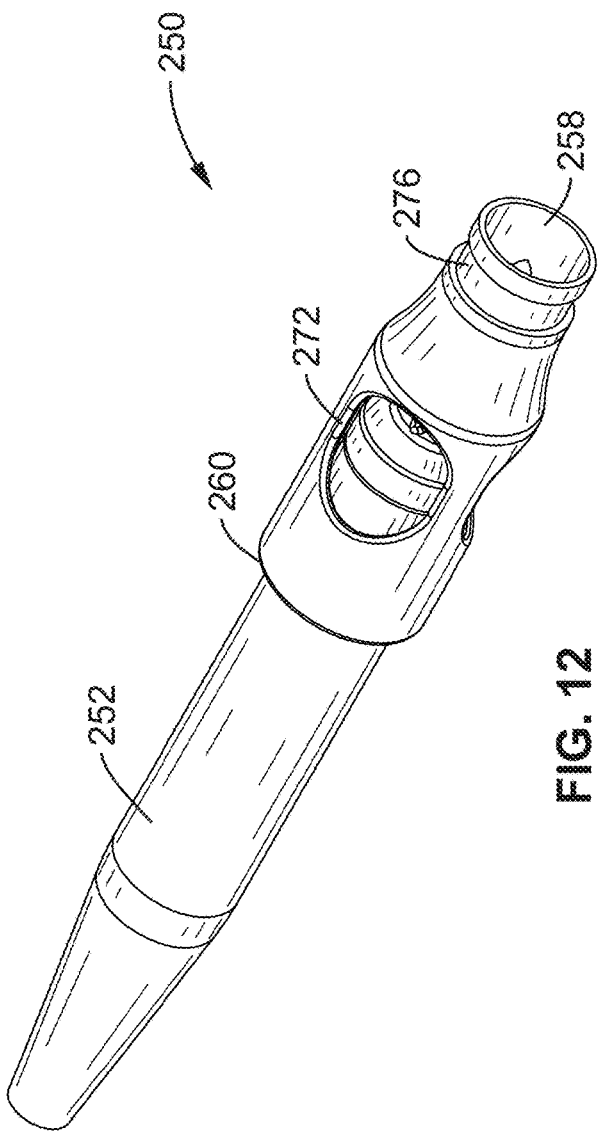

HEART ASSIST DEVICE

CROSS-REFERENCE TO RELATED APPLICATIONS

This application is a divisional of U.S. patent application Ser. No. 18/341,734 filed on Jun. 26, 2023 which is itself a continuation of U.S. patent application Ser. No. 16/920,720 filed on Jul. 5, 2020, now U.S. Pat. No. 11,724,093 issued on Jul. 26, 2023, each of which is incorporated herein by reference in its entirety, which application claims priority to, and is a 35 U.S.C. § 111 (a) continuation of, PCT international application number PCT/US2018/012736 filed on Jan. 8, 2018, also incorporated herein by reference in its entirety.

The above-referenced PCT international application was published as PCT International Publication No. WO 2019/135767 on Jul. 11, 2019, which publication is incorporated herein by reference in its entirety.

STATEMENT REGARDING FEDERALLY SPONSORED RESEARCH OR DEVELOPMENT

Not Applicable

NOTICE OF MATERIAL SUBJECT TO COPYRIGHT PROTECTION

A portion of the material in this patent document may be subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

The technology of this disclosure pertains generally to methods and devices for assisting the flow of blood through the heart, and more particularly to circulatory assist devices.

2. Background Discussion

Congestive heart failure is a major global public health problem that results in hundreds of thousands of deaths and incalculable human suffering in millions of people each year. Current treatments included modern pharmacologic agents, automatic internal defibrillators and advanced pacing devices including synchronizers. These modalities offer some symptomatic improvement and, potentially, improve survival but all are palliative treatments at best and are not curative.

Existing therapies provide limited clinical benefits for patients in advanced stages of congestive heart failure. In fact, it is estimated that several hundred thousand patients each year with far advanced CHF experience only limited clinical benefit from existing well-established treatments, and could best be served by cardiac transplantation. Cardiac transplantation offers significant improvement in symptoms and survival for patients with end stage heart failure but is available to only a few thousand patients each year due to the limited number of donor hearts.

Mechanical circulatory assistance (MCA), in the form of a total artificial heart (TAH) or a left ventricular assist device (LVAD), has the potential to meet the needs of these patients with end stage heart failure for whom there is little hope. Unfortunately, mechanical circulatory assistance has not developed into a commonly used therapy in the treatment of heart failure.

Historically, there has been substantial evolution in the technology of mechanical circulatory assistance and changes in the paradigms regarding the efficacy of MCA and its role in the treatment of heart failure. The original paradigm envisioned the development of a mass-produced pulsatile TAH that could be implanted routinely in many hundreds of thousands of end-stage patients who could otherwise benefit from cardiac transplantation. However, technical challenges have, thus far, precluded the development of the practical TAH needed to achieve the original vision.

Subsequently, it was proposed that LVADs could address the needs of most end stage patients and numerous LVADs have been developed in the last thirty years. Indeed, a number of effective LVADs have shown promise in clinical studies but have experienced only limited commercial success. Such devices include both pulsatile and rotary continuous flow pumps.

Clinical research has shown that LVADs have powerful hemodynamic effectiveness and offer substantial clinical benefit as bridges to cardiac transplantation and in treating post-cardiotomy shock. Recent experience with LVADs for destination therapy in patients who could benefit but are not candidates for cardiac transplantation, has demonstrated improvement in symptoms, quality of life and survival. Significant spontaneous recovery in left ventricular function has been observed in some bridge patients awaiting donor hearts. In some patients who experience spontaneous recovery of left ventricular function, it has been possible to remove the assist device and delay or avoid the need for cardiac transplantation.

Intravascular transvalvular ventricular assistance has been used on a limited basis in patients and has demonstrated significant clinical benefit in the setting of acute cardiogenic shock, failure to wean from cardiopulmonary bypass, assisted high risk angioplasty, and beating heart coronary revascularization. More specifically, two non-thoracotomy methods for achieving central vascular access have been previously described and have been used to a limited extent in patients. These methods are transeptal cannulation of the left atrium and transvalvular cannulation of the left ventricle.

However, previous systems exhibit very limited durability and are not generally considered practical for ambulatory or chronic clinical use.

Mechanical circulatory assistance has been shown to be an effective treatment for patients suffering from severe congestive heart failure (CHF). Both left ventricular assist devices (LVADs) and right ventricular assist devices have been adapted for bridging patients to heart transplantation and for long-term (destination) therapy. Unfortunately, existing methods for inserting these devices require major surgery during which the patient is placed on cardiopulmonary bypass and the heart may be arrested while vascular grafts are connected to a chamber of the heart to provide blood inflow to the pump of the assist system.

The implantation of existing LVADs carries too much risk to justify their customary use except in the most extreme circumstances. Current LVADs require a cardiovascular surgeon and cardiopulmonary bypass for implantation. Many previously disclosed devices and prior efforts require that both the abdominal cavity and the thoracic cavity be opened to implant the pump. Subdiaphragmatic placement of the pump necessitates diaphragmatic penetrations, which is desirable to avoid if possible.

Accordingly, left ventricular assist devices have previously been used only rarely in the treatment of CHF and then as a treatment of last resort. This is highly unfortunate, because LVADs offer greater hemodynamic efficacy than virtually all other adapted treatments, and also offer the potential of much greater clinical benefit in the treatment of congestive heart failure than other therapies and comparable to cardiac transplantation.

The substantial risk associated with present methods of implanting LVADs and RVAD has limited their use to end-stage patients. A much larger group of patients with less severe heart disease are not, presently, considered candidates for treatment with mechanical circulatory assist devices because of the substantial risk of implanting circulatory assist devices.

Thus, there remains a need for improved devices and methods that would permit less invasive cannulation of the chambers of the heart without the need for large incisions, cardiopulmonary bypass and the need to arrest the heart. This would make it possible to better serve large numbers of patients with less severe CHF.

BRIEF SUMMARY

The present disclosure, according to certain aspects, provides methods and devices for minimally and less invasive implantation of mechanical circulatory assist devices. In a preferred embodiment, the methods and devices disclosed herein are implemented in the treatment of congestive heart failure, and are installed with minimally or less invasive techniques for use as an ambulatory chronic ventricular assist device. Use of lower risk minimally or less invasive techniques would make therapeutic ventricular assistance available to class III as well as class IV congestive heart failure patients.

To overcome the barriers and shortcomings incumbent with prior efforts, various aspects of the present disclosure provide new, improved LVADs and the means for their insertion to lower the risk of their use for the treatment of congestive heart failure. The presently disclosed LVADs provide improved safety and simplicity to place in the patient, in particular with minimally and less invasive methods of insertion. According to certain embodiments, LVADs are disclosed which are adapted to be used in the treatment of congestive heart failure by the interventional cardiologist without the need for cardiac surgical support and without the need for a thoracotomy. It is believed that appropriate implementation of the presently disclosed embodiments may become the standard of care in many circumstances. The devices according to further embodiments can be inserted in much the same fashion as the implantable defibrillator, while in certain circumstances perhaps to be supplemented with the aid of a vascular surgeon.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

FIG. 1 is a sectional side view of a minimally invasive intravascular circulatory assist pump assembly having a radial motor and radial and axial bearing in accordance with the present description.

FIG. 2 is perspective view of the pump of FIG. 1.

FIG. 5 is a sectional side view of a minimally invasive intravascular circulatory assist pump assembly having an axial motor with mixed flow hydraulics in accordance with the present description.

FIG. 6 is perspective view of the pump of FIG. 5.

FIG. 9 is a sectional side view of an alternative minimally invasive intravascular circulatory assist pump assembly having a dual-sided axial motor with mixed flow hydraulics in accordance with the present description.

FIG. 10 is perspective view of the pump of FIG. 9.

FIG. 11 is a sectional side view of a minimally invasive intravascular circulatory assist pump assembly having a sealed radial motor with mixed flow hydraulics in accordance with the present description.

FIG. 12 is perspective view of the pump of FIG. 11.

DETAILED DESCRIPTION

Figure 3:
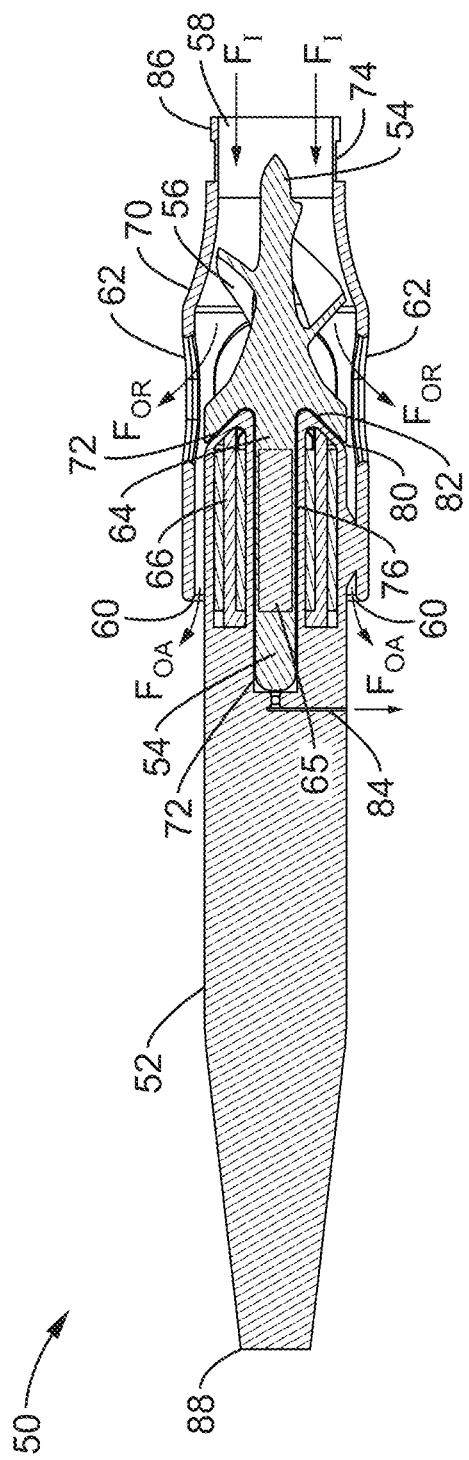
FIG. 3 is a sectional side view of a minimally invasive intravascular circulatory assist pump assembly having a radial motor with mixed flow hydraulics in accordance with the present description.

Referring more specifically to the drawings, for illustrative purposes the present technology is embodied in the apparatus generally shown in FIG. 1 through FIG. 12. It will be appreciated that the apparatus may vary as to configuration and as to details of the parts, and that the method may vary as to the specific steps and sequence, without departing from the basic concepts as disclosed herein. The devices shown in FIG. 1 to FIG. 12 show miniature heart-assist pumps as configured to improve hemocompatibility, and therefore safety, by reducing surface area of foreign materials (e.g. rotor/stator and pump housing surfaces) that are exposed to blood. While miniaturizing the design, torque is maintained (conservation of energy) to maintain sustainable flow and pressure capacity. Key factors in hemocompatibility are reducing shear stress and exposure time. To improve hemocompatibility one or both should be reduced. As such, a pump may have low shear stress, but significant exposure times to those stresses.

Referring first to the embodiment shown in FIG. 1 and FIG. 2, FIG. 1 shows a sectional side view of a minimally invasive intravascular circulatory assist pump assembly 10 having a radial motor and radial and axial bearing in accordance with the present description. FIG. 2 is perspective view of the pump assembly 10 of FIG. 1.

Pump assembly 10 comprises a pump housing 12 with first and second ends 46, 48, respectively, and a rotor 14 configured to be rotatably disposed within the housing 12.

These components are configured in a particular manner relative to each other as follows.

Housing 12 includes an axial inlet at end 46 leading to first cylindrical bore 18 configured for housing an impeller 16 of the rotor 14. The impeller generally comprises a plurality of helical sweeping blades. The housing 12 may also comprise helical stator (diffuser) blades 20 coupled to the inner bore 18. While a specific configuration and relative arrangement of such impeller blades 16 and stator blades 20 shown in FIG. 1 is considered of beneficial use, other configurations may be employed as would be apparent to one of ordinary skill. In this configuration, the rotor shaft 45 comprises the hub that rotates between the stator blades 20. The combination of the cylindrical bore 18 and impeller 16 operate as a pumping chamber configured to draw blood flow into $F_I$ the bore 18.

The housing 12 has a first section 30 starting at end 46 and extending axially toward, but short of, end 48 of the housing 12. First housing section 30 has a larger diameter than the diameter of the remainder of the housing 12 terminating at end 48, such that the first section 30 forms an annular opening 22 in communication with and at the far end of cylindrical bore 18. Annular opening 22 forms an axially oriented outlet for an axial outlet flow $F_O$ out of the cylindrical bore or pumping chamber 18.

The elongate shaft 45 of rotor 16 is disposed within a second cylindrical bore 40 concentric with cylindrical bore 18. Cylindrical bore 40 is sized such that it forms the mating inner bearing surface to the outer bearing surface of rotor shaft 45 via a journal bearing fit between the two surfaces. For purposes of this description, the terms "cylindrical bore 40" and "inner bearing surface" are used interchangeably. Thus, the cylindrical bore 40 and the bearing surface of rotor shaft 45 form a hydrodynamic journal bearing, also sometimes referred to as a "fluid" bearing, or "mechanical" bearing or bushing. The formed hydrodynamic bearing is a function of the spacing between the rotor shaft bearing surface and the inner bearing surface, which along at least a substantial portion of the length of the rotor shaft 45 comprises an annular gap or leak path 32 for blood to lubricate and flow within the bearing.

During normal operation of the pump assembly 10 as shown in the operating configuration of FIG. 1, rotational motion of the rotor 14 within housing 12 is generally achieved via a magnetically driven radial motor or actuator comprising a rotor magnet 28 and a rotor stator disposed within bearing surfaces of the rotor shaft 45 and housing 12, respectively. The solid rotor shaft 45 houses one or more rotor magnets 28 that interact with motor stator 26. Motor stator 26 comprises an electrically conductive coil (not shown) that is adapted to be coupled to a power source (not shown) via leads, and is positioned relative to the rotor magnet 28 to form a flux gap motor interface such that, in an operating mode upon activation by the power source, electrical current flowing through the motor stator 26 coil creates a magnetic flux field that extends across a flux gap clearance (i.e. leakage path 32) between the rotor 14 and housing 12 and that displaces the rotor magnet 28 sufficient to torque the rotor 14 and rotate the rotor 14 within the journal bearing clearance cylindrical bore 40. It is also appreciated that the motor stator coil 26 may be axially offset with respect to the rotor magnet 28 to form an axial force or preload of the rotor shaft 45 into the bore 40 of the housing.

Upon rotation of the rotor 14 within the pump housing 12, the impeller 16 draws blood flow $F_I$ inward from the axial inlet port 24 at end 46 and into the pumping chamber defined by cylindrical bore 18. Blood is directed into the axial inlet port 24 in-line with respect to the longitudinal axis of the rotor shaft 45 and cylindrical bores 18, 40. Thus, the direction of the inlet flow of blood $F_I$ and outlet flow of blood $F_O$ are primarily axial. Axial inlet port 24 may be coupled to a first end of cannula (not shown) with the pump 10 located at a first location of the circulatory system, wherein the output flow $F_o$ is dispersed into the first end of cannula for distributing the output flow of blood to a second end of the cannula at a second location in the circulatory system. It is also appreciated that the flow of blood as shown in FIG. 1 may be reversed (e.g. via reversing direction of impeller 16 or orientation of impeller blades) such that annular aperture 22 is an input, and axial port 24 at end 46 is an output.

Radial support of the rotor 14 is provided by the action of the relative motion between the outer bearing surface of the rotor shaft 45 and the inner bearing surface of cylindrical bore 40 of the pump housing 12. This produces a hydrodynamic radial or journal bearing. In particular, hydrodynamic thrust forces generated by the relative motion of the rotor 14 with respect to the inner bearing surface are the primary or sole source of radial suspension of the rotor within the cylindrical bore 40. The journal bearing is sized to form an annular gap (leak path) 32 that is a function of the outer diameter of the rotor shaft 45 and the inner diameter of the bore 40. In a preferred embodiment, the annular gap is sized to be between 0.002 in.-0.003 in. It is appreciated that the image of FIG. 1 shows a much larger gap for leakage path 32 (respective to the other component dimensions), primarily for illustrating purposes in showing the flow characteristics of the pump 10.

The journal bearing construction beneficially minimizes shear stress and concurrently with output flow $F_O$ and axial input flow $F_I$, promotes leakage flow $F_L$ from the axial leakage inlet at the entrance of bore 40 rearward toward the hemispherical end 36 of rotor 14 and eventually out radial ports 34. Leakage flow $F_L$ is driven by geometry (i.e. pumping grooves) on the rotor 14. The direction of leak path flow $F_L$ can be reversed (from that depicted in this embodiment) based on the rotor 14 geometry.

All mating surfaces are preferably continual relative motion along the communicative leakage path 32. All such tight clearance, low flow surfaces are thus continuously washed with motion. This optimizes hemocompatibility by minimizing negative physiological impacts such as hemolysis and thrombosis. In particular, hemolysis is minimized because $F_I \gg F_L$. Other hemocompatibility factors, e.g. von Willebrand factor, platelet activation, etc., may also be positively influenced. The active leakage flow path 32 through moving parts allows active washing of exposed surfaces within the bore 40. This relieves the requirement for seals, which typically aggravate thrombus formation, and thus the present embodiments enhance longevity as an implant.

In a preferred embodiment, the bearing surfaces of the rotor shaft 45 and cylindrical bore 40, and other similar bearing surfaces disclosed in the various embodiments below, may comprise one or more of a radial bearing and/or hemispherical/axial bearing (both not shown) within the leak path 32 through the motor, as shown in PCT international application number PCT/US16/30445, filed on May 2, 2016, to provide additional stability and flow characteristics to the rotor 14. In one embodiment, a portion of the cylindrical surface of the rotor shaft 45 may comprise a tri-lobed radial bearing that generally comprises three lands (not shown)

extending outward from a base-diameter section (not shown), with a taper (not shown) that transitions each land and base-diameter section.

The rotor 14 may also incorporate a grooved hemispherical thrust bearing (not shown) disposed at hemispherical end 36 of rotor 14. In one configuration, the axial thrust bearing comprises three swept-tapered grooves (not shown). The thrust bearing interface 39 of rotor end 36 with cupped inner bore surface 38 is configured to provide a pressure differential and accordingly pumping mechanism to promote flow through leakage path 32. The grooves are deepest near the center of the rotor in a shallow-deep-shallow configuration sweeping from center outward (radially). The thrust bearing creates a low pressure region that is lowest at the distal tip where the depth is transitioning from shallow to deep, and highest at the groove exit, providing significant radial stability. This pressure produces an axial distributed thrust, promoting flow into the leakage path 32, while also providing radial stability as well.

It is also appreciated that the hemispherical thrust bearing 39 and/or radial bearing may also be configured to reverse the flow of blood $F_L$ in the leak path 32 such that blood enters radial ports 34 and flows retrograde within the leak path 32 to exit out of the bore 40 toward the front end 46 of the housing.

A radial step 42 may be incorporated to support coupling of a cannula (not shown) or other conduit.

Figure 4:
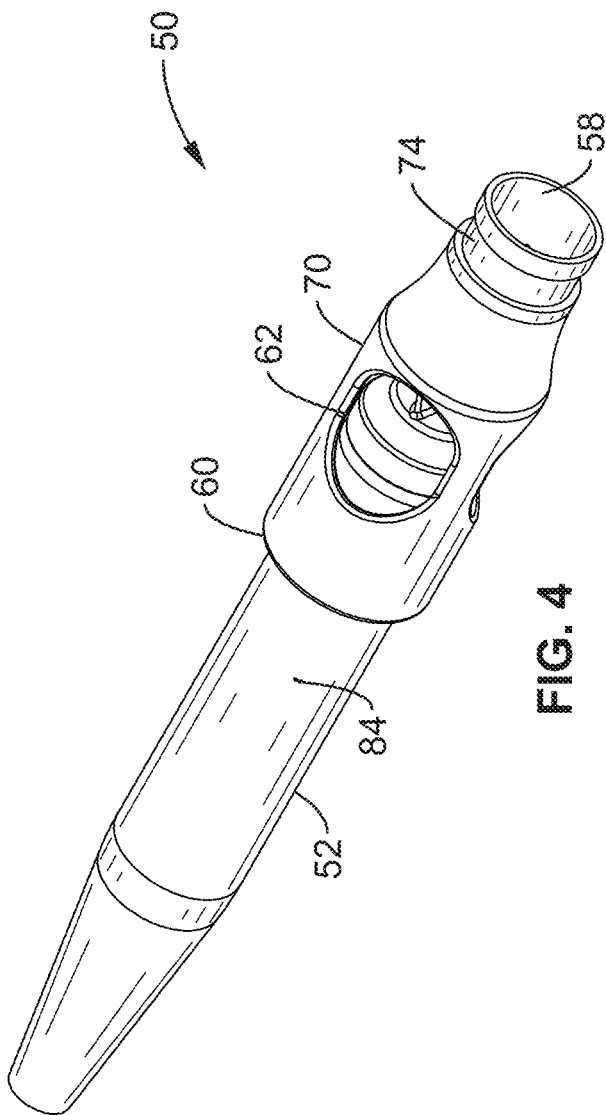
FIG. 4 is perspective view of the pump of FIG. 3.

Referring next to the embodiment shown in FIG. 3 and FIG. 4, FIG. 3 shows a sectional side view of a minimally invasive intravascular circulatory assist pump assembly 50 having a radial motor with mixed flow hydraulics in accordance with the present description. FIG. 4 is perspective view of the pump assembly 50 of FIG. 3.

Pump assembly 50 comprises a pump housing 52 with first and second ends 86, 88, respectively, and a rotor 54 configured to be rotatably disposed within the housing 52. These components are configured in a particular manner relative to each other as follows.

Housing 52 includes an axial inlet at end 86 leading to central bore 58 configured for housing an impeller 56 of the rotor 54. The impeller 56 generally comprises a plurality of helical sweeping blades. Unlike the embodiment of FIG. 1, pump assembly 50 incorporates mixed-flow hydraulics having rotor blades only, i.e. no stator blades. While the specific configuration and relative arrangement of such impeller blades 56 shown in FIG. 3 is considered of beneficial use, other configurations may be employed as would be apparent to one of ordinary skill. In this configuration, the bore 58 has an increasing cross-section or diameter from end 86 toward the impeller blades 56. The combination of the central bore 58 and impeller 56 operate as a pumping chamber configured to draw blood flow $F_I$ into the central bore 58.

The housing 52 has a first section 70 starting at end 86 and extending axially toward, but short of, end 88 of the housing 52. First housing section 70 terminates distally at a larger diameter than the diameter of the remainder of the housing 52, such that the first section 70 forms an annular opening 60 in communication with and at the far end of central bore 58. Annular opening 60 forms an axially oriented outlet for an axial outlet flow $F_{OA}$ out of the cylindrical bore or pumping chamber 58. Furthermore, blood flow $F_{OR}$ is directed radially outward from the central bore 58 via a plurality of radial ports 62. For purposes of this discussion, "radial port" is herein defined to be a port having at least a radial component with respect to direction of flow. The configuration of pump 50 is shown in FIG. 3 and FIG. 4 as having 3 radial ports 62 in housing 52. However, it is appreciated that any number of ports may be included.

Opposite from impeller 56, the rotor 54 comprises cupped-conical bearing surface 82 and a rotor shaft 64 that is configured to be disposed within a cylindrical bore 76. Cylindrical bore 76 is sized such that it forms the mating inner bearing surface to the outer bearing surface of rotor shaft 64 via a journal bearing fit between the two surfaces. Thus, the cylindrical bore 76 and the bearing surface of rotor shaft 64 form a hydrodynamic journal bearing. The formed hydrodynamic bearing is a function of the spacing between the rotor shaft bearing surface and the inner bearing surface, which along at least a substantial portion of the length of the rotor shaft 64 comprises an annular gap or leak path 72 for blood to lubricate and flow within the bearing. Leak path 72 starts at the conical bearing entrance formed between cupped-conical surface 82 of the rotor 54 and the opposing conical surface 80 of the housing 52, and extends along the length of the rotor shaft 64/cylindrical bore 76 interface, terminating at radial outlet port 84.

During normal operation of the pump assembly 50 as shown in the operating configuration of FIG. 3, rotational motion of the rotor 54 within housing 52 is generally achieved via a magnetically driven radial motor or actuator comprising a rotor magnet 65 and a rotor stator 66 disposed within bearing surfaces of the rotor shaft 64 and housing 52, respectively. The solid rotor shaft 64 houses one or more rotor magnets that interact with motor stator 66. Motor stator 66 comprises an electrically conductive coil (not shown) that is adapted to be coupled to a power source (not shown) via leads, and is positioned relative to the rotor magnet to form a flux gap motor interface such that, in an operating mode upon activation by the power source, electrical current flowing through the motor stator 66 coil creates a magnetic flux field that extends across a flux gap clearance (i.e. leakage path 72) between the rotor 54 and housing 52 and that displaces the rotor magnet sufficient to torque the rotor 54 and rotate the rotor 54 within the journal bearing clearance cylindrical bore 76. It is also appreciated that the motor stator coil 66 may be axially offset with respect to the rotor magnet to form an axial force or preload of the rotor shaft 64 into the bore 76 of the housing.

Upon rotation of the rotor 54 within the pump housing 52, the impeller 56 draws blood flow $F_I$ inward from the axial inlet at end 86 and into the pumping chamber defined by central bore 58. Blood is directed into the axial port in-line with respect to the longitudinal axis of the rotor shaft 64 and cylindrical bore 76. The direction of the inlet flow of blood $F_I$ and outlet flow of blood $F_{OA}$ are primarily axial, while radial outlet flow $F_{OR}$ has at least a significant radial component. The axial port at end 86 may be coupled to a first end of cannula (not shown) with the pump 50 located at a first location of the circulatory system, wherein the output flow $F_o$ is dispersed into the first end of cannula for distributing the output flow of blood to a second end of the cannula at a second location in the circulatory system. It is also appreciated that the flow of blood as shown in FIG. 3 may be reversed (e.g. via reversing direction of impeller 56 or orientation of impeller blades) such that annular aperture 60 and ports 62 are inputs, and axial port at end 86 is an output.

Radial support of the rotor 14 is provided by the conical bearing and action of the relative motion between the outer bearing surface of the rotor shaft 64 and the inner bearing surface of cylindrical bore 76. This produces a hydrodynamic radial or journal bearing. In particular, hydrodynamic thrust forces generated by the relative motion of the rotor 54 with respect to the inner bearing surface are the primary or sole source of radial suspension of the rotor within the cylindrical bore 76. The journal bearing is sized to form an annular gap 72 between the outer diameter of the rotor shaft 64 and the inner diameter of the bore 76. In a preferred embodiment, the annular gap is sized to be between 0.002 in.-0.003 in.

Leakage flow $F_L$ is driven by geometry (i.e. pumping grooves) on the rotor 54. The direction of leak path flow $F_L$ can be reversed (from that depicted in this embodiment) based on the rotor 54 geometry.

All mating surfaces are preferably continual relative motion along the communicative. All such tight clearance, low flow surfaces along leakage path 72 are continuously washed with motion, and hemolysis and thrombosis, or other negative physiological impacts, can be minimized because $F_I \gg F_L$. The active leakage flow path 72 through moving parts allows active washing of exposed surfaces within the bore 76 and conical bearing.

In a preferred embodiment, the bearing surfaces of the rotor shaft 64 and cylindrical bore 76 may comprise a radial bearing (not shown) and conical hydrodynamic bearing within the leak path 76 through the motor, as provided in PCT international application number PCT/US16/30445, filed on May 2, 2016, to provide additional stability and flow characteristics to the rotor 54. In one embodiment, a portion of the cylindrical surface of the rotor shaft 64 may comprise a tri-lobed radial bearing that generally comprises three lands (not shown) extending outward from a base-diameter section (not shown), with a taper (not shown) that transitions each land and base-diameter section.

The rotor 54 may also incorporate a conical thrust bearing that is formed via conical surfaces 82 and 80 of the rotor 54 and housing 52 respectively. In this configuration, the axial thrust bearing comprises three longitudinally oriented grooves (not shown) that transverse radially outward from the shaft 64. The thrust bearing is configured to provide a pressure differential and accordingly pumping mechanism to promote flow through leakage path 72. The conical bearing is similar to the hemispherical bearing in that it can generate both radial and axial forces/pressures with a single set of grooves/features. In some embodiments, a conical axial bearing design may include tapered-land grooves (not shown) in place of or in addition to longitudinal grooves.

A radial flange 74 may also be incorporated at end 86 to support coupling of a cannula (not shown) or other conduit.

Referring next to the embodiment shown in FIG. 5 and FIG. 6, FIG. 5 shows a sectional side view of a minimally invasive intravascular circulatory assist pump assembly 100 having an axial motor with mixed flow hydraulics in accordance with the present description. FIG. 6 is perspective view of the pump assembly 100 of FIG. 5. The axial motor configuration of FIG. 5 and FIG. 6 reduces the axial length generally present in the radial motor and internal journal bearing configuration.

Pump assembly 100 comprises a pump housing 102 with first and second ends 136, 138, respectively, and a rotor 104 configured to be rotatably disposed within the housing 102. These components are configured in a particular manner relative to each other as follows.

Housing 102 includes an axial inlet at end 136 leading to central bore 108 configured for housing an impeller 106 of the rotor 104. The impeller 106 generally comprises a plurality of helical sweeping blades. Unlike the embodiment of FIG. 1, pump assembly 100 incorporates mixed-flow hydraulics having rotor blades only. While the specific configuration and relative arrangement of such impeller blades 106 shown in FIG. 5 is considered of beneficial use, other configurations may be employed as would be apparent to one of ordinary skill. In this configuration, the bore 108 has an increasing cross-section or diameter from end 136 toward the impeller blades 106. The combination of the central bore 108 and impeller 106 operate as a pumping chamber configured to draw blood flow $F_I$ into the central bore 108.

The housing 102 has a first section 120 starting at end 136 and extending axially toward, but short of, end 138 of the housing 102. First housing section 120 terminates distally at a larger diameter than the diameter of the remainder of the housing 102, such that the first section 120 forms an annular opening 110 in communication with and at the far end of central bore 108. Annular opening 110 forms an axially oriented outlet for an axial outlet flow $F_{OA}$ out of the cylindrical bore or pumping chamber 108. Furthermore, blood flow $F_{OR}$ is directed radially outward from the central bore 108 via a plurality of radial ports 112. The configuration of pump 100 is shown in FIG. 5 and FIG. 6 as having 3 radial ports 112 in housing 102. However, it is appreciated that any number of ports may be included.

Opposite from impeller 106, the rotor 104 comprises cupped-conical bearing surface 122 configured to mate with conical surface 124 of the housing 102 via a journal bearing fit between the two surfaces to form a hydrodynamic journal bearing. The formed hydrodynamic bearing is a function of the spacing between the cupped-conical bearing surface 122 configured to mate with conical surface 124, which comprises a gap or leak path 126 for blood to lubricate and flow within the bearing.

During normal operation of the pump assembly 100 as shown in the operating configuration of FIG. 5, rotational motion of the rotor 104 within housing 102 is generally achieved via a magnetically driven axial motor or actuator comprising one or more rotor magnets 114 and a rotor stator 116 disposed within bearing surfaces of the rotor 104 and housing 102, respectively. Motor stator 116 comprises an electrically conductive coil (not shown) that is adapted to be coupled to a power source (not shown) via leads, and is positioned relative to the rotor magnet to form a flux gap motor interface such that, in an operating mode upon activation by the power source, electrical current flowing through the motor stator 116 coil creates a magnetic flux field that extends across a flux gap clearance (i.e. leakage path 126) between the rotor 104 and housing 102 and that displaces the rotor magnet sufficient to torque the rotor 104 and rotate the rotor 104 within the journal bearing clearance.

Upon rotation of the rotor 104 within the pump housing 102, the impeller 106 draws blood flow $F_I$ inward from the axial inlet at end 136 and into the pumping chamber defined by central bore 108. Blood is directed into the axial port in-line with respect to the longitudinal or rotational axis of the rotor 104. The direction of the inlet flow of blood $F_I$ and outlet flow of blood $F_{OA}$ are primarily axial, while radial outlet flow $F_{OR}$ has at least a significant radial component. The axial port at end 136 may be coupled to a first end of cannula (not shown) with the pump 100 located at a first location of the circulatory system, wherein the output flow $F_O$ is dispersed into the first end of cannula for distributing the output flow of blood to a second end of the cannula at a second location in the circulatory system. It is also appreciated that the flow of blood as shown in FIG. 5 may be reversed (e.g. via reversing direction of impeller 106 or orientation of impeller blades) such that annular aperture 110 and ports 112 are inputs, and axial port at end 136 is an output.

Radial support of the rotor 104 is provided by the hydrodynamic conical bearing and action of the relative motion between the bearing surfaces 122 and 124. This produces a hydrodynamic radial or journal bearing. In particular, hydrodynamic thrust forces generated by the relative motion of the rotor 104 with respect to the inner bearing surface are the primary or sole source of radial suspension of the rotor within the central bore 108. The journal bearing is sized to form a gap or leak path 126 sized to be between 0.002 in.-0.003 in.

Leakage flow within the leak path 126 is driven by geometry (i.e. pumping grooves) on the rotor 104 or housing 102. The direction of leak path flow can be reversed based on the rotor 104 geometry. All such tight clearance, low flow surfaces along leakage path 126 are continuously washed with motion, and hemolysis and thrombosis can be minimized as the active leakage flow path 126 through moving parts allows active washing of exposed surfaces.

In a preferred embodiment, the bearing surfaces comprise a conical hydrodynamic bearing within the leak path 126 through the motor, as provided in PCT international application number PCT/US16/30445, filed on May 2, 2016, to provide additional stability and flow characteristics to the rotor 104. The conical thrust bearing is formed via conical surfaces 122, 124 of the rotor 104 and housing 102. In this configuration, the axial thrust bearing comprises three longitudinally oriented grooves (not shown) that transverse radially outward from the center of the rotor 104. The thrust bearing is configured to provide a pressure differential and accordingly pumping mechanism to promote flow through leakage path 126. The conical bearing is similar to the hemispherical bearing in that it can generate both radial and axial forces/pressures with a single set of grooves/features. In some embodiments, a conical axial bearing design may include tapered-land grooves (not shown) in place of or in addition to longitudinal grooves.

A radial flange 130 may also be incorporated at end 136 to support coupling of a cannula (not shown) or other conduit.

Figure 7:
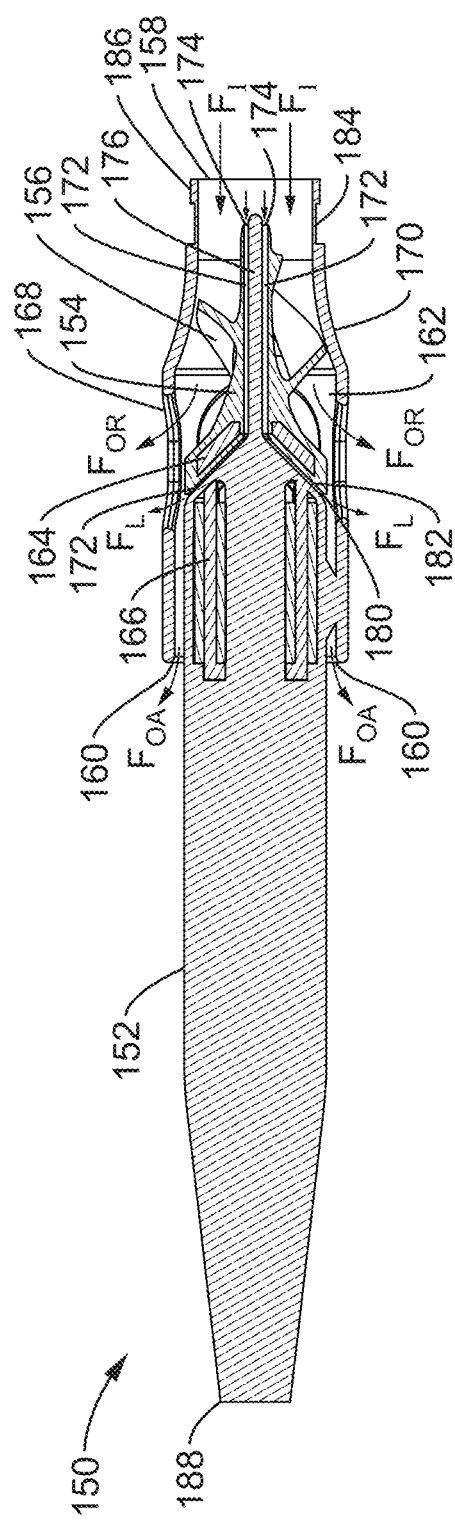
FIG. 7 is a sectional side view of an alternative minimally invasive intravascular circulatory assist pump assembly having an axial motor with mixed flow hydraulics in accordance with the present description.
Figure 8:
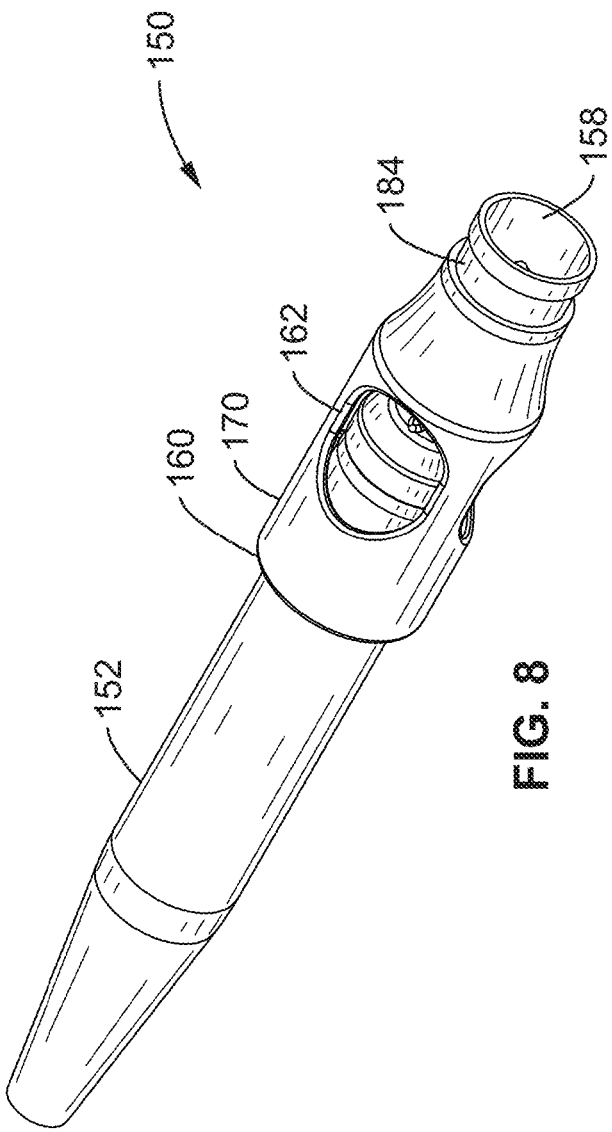
FIG. 8 is perspective view of the pump of FIG. 7.

Referring next to the embodiment shown in FIG. 7 and FIG. 8, FIG. 7 shows a sectional side view of an alternative minimally invasive intravascular circulatory assist pump assembly 150 having an axial motor with mixed flow hydraulics in accordance with the present description. FIG. 8 is perspective view of the pump assembly 150 of FIG. 7.

Pump assembly 150 comprises a pump housing 152 with first and second ends 186, 188, respectively, and a rotor 154 configured to be rotatably disposed within the housing 152. These components are configured in a particular manner relative to each other as follows.

Housing 152 includes an axial inlet at end 186 leading to central bore 158 configured for housing an impeller 156 of the rotor 154. The impeller 156 generally comprises a plurality of helical sweeping blades. Unlike the embodiment of FIG. 1, pump assembly 150 incorporates mixed-flow hydraulics having rotor blades only. While the specific configuration and relative arrangement of such impeller blades 106 shown in FIG. 7 is considered of beneficial use, other configurations may be employed as would be apparent to one of ordinary skill. In this configuration, the bore 158 has an increasing cross-section or diameter from end 186 toward the impeller blades 106. The combination of the central bore 158 and impeller 156 operate as a pumping chamber configured to draw blood flow $F_I$ into the central bore 158.

The housing 152 has a first section 170 starting at end 186 and extending axially toward, but short of, end 188 of the housing 152. First housing section 170 terminates distally at a larger diameter than the diameter of the remainder of the housing 152, such that the first section 170 forms an annular opening 160 in communication with and at the far end of central bore 108. Annular opening 160 forms an axially oriented outlet for an axial outlet flow $F_{OA}$ out of the cylindrical bore or pumping chamber 158. Furthermore, blood flow $F_{OR}$ is directed radially outward from the central bore 158 via a plurality of radial ports 162. The configuration of pump 150 is shown in FIG. 7 and FIG. 8 as having 3 radial ports 162 in housing 152. However, it is appreciated that any number of ports may be included.

Opposite from impeller 156, the rotor 154 comprises cupped-conical bearing surface 182 configured to mate with conical surface 180 of the housing 152 and a cylindrical bore 174 fit around cylindrical shaft 176 of the housing via a journal bearing fit between the corresponding surfaces to form a hydrodynamic journal bearing. The formed hydrodynamic bearing is a function of the spacing between the cupped-conical bearing surface 182 configured to mate with conical surface 180, and cylindrical bore 174 fit around cylindrical shaft 176, which form a contiguous gap or leak path 172 for blood to lubricate and flow within the bearing.

During normal operation of the pump assembly 150 as shown in the operating configuration of FIG. 7, rotational motion of the rotor 154 within housing 152 is generally achieved via a magnetically driven axial motor or actuator comprising one or more rotor magnets 164 and a rotor stator 166 disposed within bearing surfaces of the rotor 154 and housing 152, respectively. Motor stator 166 comprises an electrically conductive coil (not shown) that is adapted to be coupled to a power source (not shown) via leads, and is positioned relative to the rotor magnet to form a flux gap motor interface such that, in an operating mode upon activation by the power source, electrical current flowing through the motor stator 166 coil creates a magnetic flux field that extends across a flux gap clearance (i.e. leakage path 172) between the rotor 154 and housing 152 and that displaces the rotor magnet sufficient to torque the rotor 154 and rotate the rotor 154 within the journal bearing clearance.

Upon rotation of the rotor 154 within the pump housing 152, the impeller 156 draws blood flow $F_I$ inward from the axial inlet at end 186 and into the pumping chamber defined by central bore 158. Blood is directed into the axial port in-line with respect to the longitudinal or rotational axis of the rotor 154. The direction of the inlet flow of blood $F_I$ and outlet flow of blood $F_{OA}$ are primarily axial, while radial outlet flow $F_{OR}$ has at least a significant axial component. The axial port at end 186 may be coupled to a first end of cannula (not shown) with the pump 150 located at a first location of the circulatory system, wherein the output flow $F_O$ is dispersed into the first end of cannula for distributing the output flow of blood to a second end of the cannula at a second location in the circulatory system. It is also appreciated that the flow of blood as shown in FIG. 7 may be reversed (e.g. via reversing direction of impeller 156 or orientation of impeller blades) such that annular aperture 160 and ports 162 are inputs, and axial port at end 186 is an output.

Radial support of the rotor 154 is provided by the hydrodynamic conical bearing and action of the relative motion between the bearing surfaces 122 and 124, and the outer bearing surface of the housing shaft 176 and the inner bearing surface of cylindrical bore 174. This produces a hydrodynamic radial or journal bearing. In particular, hydrodynamic thrust forces generated by the relative motion of the rotor 154 with respect to the inner bearing surface are the primary or sole source of radial suspension of the rotor over the housing shaft 176. The journal bearing is sized to form a gap or leak path 172 sized to be between 0.002 in.-0.003 in.

Leakage flow within the leak path 172 is driven by geometry (i.e. pumping grooves) on the rotor 154 or housing 152. The direction of leak path flow can be reversed based on the rotor 154 geometry. All such tight clearance, low flow surfaces along leakage path 172 are continuously washed with motion, and hemolysis and thrombosis can be minimized as the active leakage flow path 172 through moving parts allows active washing of exposed surfaces.

In a preferred embodiment, the bearing surfaces comprise a radial bearing (not shown) and conical hydrodynamic bearing within the leak path 172 through the motor, as provided in PCT international application number PCT/US16/30445, filed on May 2, 2016, to provide additional stability and flow characteristics to the rotor 154. The conical thrust bearing is formed via conical surfaces 182 and 180 of the rotor 154 and housing 152 respectively. In this configuration, the axial thrust bearing comprises three longitudinally oriented grooves (not shown) that transverse radially outward from the center of the rotor 154. The thrust bearing is configured to provide a pressure differential and accordingly pumping mechanism to promote flow through leakage path 172. The conical bearing is similar to the hemispherical bearing in that it can generate both radial and axial forces/pressures with a single set of grooves/features. In some embodiments, a conical axial bearing design may include tapered-land grooves (not shown) in place of or in addition to longitudinal grooves.

A radial flange 184 may also be incorporated at end 186 to support coupling of a cannula (not shown) or other conduit.

Referring next to the embodiment shown in FIG. 9 and FIG. 10, FIG. 9 is a sectional side view of a minimally invasive intravascular circulatory assist pump assembly 200 having a dual-sided axial motor with mixed flow hydraulics in accordance with the present description. FIG. 10 is perspective view of the pump 200 of FIG. 9.

Pump assembly 200 comprises a pump housing 202 with first and second ends 236, 238, respectively, and a rotor 204 configured to be rotatably disposed within the housing 202. These components are configured in a particular manner relative to each other as follows.

Housing 202 includes an axial inlet at end 236 leading to central bore 208 configured for housing an impeller 206 of the rotor 204. The impeller 206 generally comprises a plurality of helical sweeping blades. Pump assembly 200 incorporates mixed-flow hydraulics having rotor blades only. While the specific configuration and relative arrangement of such impeller blades 206 shown in FIG. 9 is considered of beneficial use, other configurations may be employed as would be apparent to one of ordinary skill. In this configuration, the bore 208 has an increasing cross-section or diameter from end 236 toward the impeller blades 206. The combination of the central bore 208 and impeller 206 operate as a pumping chamber configured to draw blood flow F into the central bore 208.

The housing 202 has a first section 220 starting at end 136 and extending axially toward, but short of, end 238 of the housing 202. First housing section 220 terminates distally at a larger diameter than the diameter of the remainder of the housing 202, such that the first section 220 forms an annular opening 210 in communication with and at the far end of central bore 208. Annular opening 210 forms an axially oriented outlet for an axial outlet flow $F_{OA}$ out of the cylindrical bore or pumping chamber 208. Furthermore, blood flow $F_{OR}$ is directed radially outward from the central bore 208 via a plurality of radial ports 212. The configuration of pump 200 is shown in FIG. 9 and FIG. 10 as having 3 radial ports 212 in housing 202. However, it is appreciated that any number of ports may be included.

Opposite from impeller 206, the rotor 204 comprises cupped-conical bearing 230 similar to the cupped conical surfaces 80 and 82 shown in FIG. 3. A rotor shaft 224 is disposed on the distal side of bearing cupped-conical bearing 230 and is disposed within a cylindrical bore 226. Cylindrical bore 226 is sized such that it forms the mating inner bearing surface to the outer bearing surface of rotor shaft 224 via a journal bearing fit between the two surfaces, as detailed above. A second opposing cupped-conical bearing 231 is disposed on the opposite side of the shaft 224 from the first cupped-conical bearing 230. In a preferred embodiment, a leak path 232 and corresponding hydrodynamic bearing is formed through two of the three bearing surfaces, including conical bearings 230, 231, and the cylindrical bearing formed from the shaft 224/cylindrical bore 226 interface. For example, both conical bearing interfaces 230, 231 may be hydrodynamic bearings, in which the shaft 224/cylindrical bore 226 interface is a more open gap so as to be non-hydrodynamic. Alternatively, one of the conical bearing interfaces 230, 231 may be hydrodynamic bearings may be hydrodynamic bearings, along with the shaft 224/cylindrical bore 226 interface.

The formed hydrodynamic bearing is a function of the spacing between the rotor shaft bearing surface and the inner bearing surface, e.g. of the cylindrical bore 226 and opposing conical surfaces of housing 202 and a specified gap to lubricate and flow within the bearing. Leak path 232 starts at the conical bearing entrance formed at conical bearing 230, and extends along the length of the rotor shaft 224/cylindrical bore 226 interface, through second conical bearing 231, and terminating at radial outlet port 234. During operation, all low flow surfaces along leakage path 232 are continuously washed with motion, and hemolysis and thrombosis can be minimized because $F_J \gg F_L$. The active leakage flow path 232 through moving parts allows active washing of exposed surfaces within the bore 232 and conical bearings.

During normal operation of the pump assembly 200 as shown in the operating configuration of FIG. 9, rotational motion of the rotor 204 within housing 202 is generally achieved via a magnetically driven dual-sided axial motor or actuator. The dual-sided axial motor comprises rotor magnets 214 disposed in both sides of the rotor 204 parallel to the conical bearing 230/231 interfaces, and a rotor stator 216 disposed within bearing surfaces of the housing 202. Motor stator 216 comprises an electrically conductive coil (not shown) that is adapted to be coupled to a power source (not shown) via leads, and is positioned relative to the rotor magnet to form a flux gap motor interface such that, in an operating mode upon activation by the power source, electrical current flowing through the motor stator 216 coil creates a magnetic flux field that extends across a flux gap clearance (i.e. leakage path 232) between the rotor 204 and housing 202 and that displaces the rotor magnet sufficient to torque the rotor 204 and rotate the rotor 204 within the journal bearing clearance.

Upon rotation of the rotor 204 within the pump housing 202, the impeller 206 draws blood flow $F_I$ inward from the axial inlet at end 236 and into the pumping chamber defined by central bore 208. Blood is directed into the axial port in-line with respect to the longitudinal axis of the rotor shaft 224 and cylindrical bore 226. The direction of the inlet flow of blood $F_I$ and outlet flow of blood $F_{OA}$ are primarily axial, while radial outlet flow $F_{OR}$ has at least a significant axial component. The axial port at end 236 may be coupled to a first end of cannula (not shown) with the pump 200 located at a first location of the circulatory system, wherein the output flow $F_o$ is dispersed into the first end of cannula for distributing the output flow of blood to a second end of the cannula at a second location in the circulatory system. It is also appreciated that the flow of blood as shown in FIG. 9 may be reversed (e.g. via reversing direction of impeller 206 or orientation of impeller blades) such that annular aperture 210 and ports 212 are inputs, and axial port at end 236 is an output.

Leakage flow $F_L$ is driven by geometry (i.e. pumping grooves) on the rotor 204. The direction of leak path flow $F_L$ can be reversed (from that depicted in this embodiment) based on the rotor 204 geometry.

In a preferred embodiment, the bearing surfaces of the rotor shaft 224 and cylindrical bore 226 may comprise a radial bearing (not shown) and conical hydrodynamic bearing within the leak path 232 through the motor, as provided in PCT international application number PCT/US16/30445, filed on May 2, 2016, to provide additional stability and flow characteristics to the rotor 204. In one embodiment, a portion of the cylindrical surface of the rotor shaft 224 may comprise a tri-lobed radial bearing that generally comprises three lands (not shown) extending outward from a base-diameter section (not shown), with a taper (not shown) that transitions each land and base-diameter section.

The rotor 204 may also incorporate a conical thrust bearing that is formed via conical surfaces 230 and 231. In this configuration, the axial thrust bearing comprises three longitudinally oriented grooves (not shown) that transverse radially outward from the shaft 224. The thrust bearing is configured to provide a pressure differential and accordingly pumping mechanism to promote flow through leakage path 232. The conical bearing is similar to the hemispherical bearing in that it can generate both radial and axial forces/pressures with a single set of grooves/features. In some embodiments, a conical axial bearing design may include tapered-land grooves (not shown) in place of or in addition to longitudinal grooves.

A radial flange 222 may also be incorporated at end 236 to support coupling of a cannula (not shown) or other conduit.

Referring next to the embodiment shown in FIG. 11 and FIG. 12, FIG. 11 is a sectional side view of a minimally invasive intravascular circulatory assist pump assembly 250 having a sealed radial motor with mixed flow hydraulics in accordance with the present description. FIG. 12 is perspective view of the pump 250 of FIG. 11.

Pump assembly 250 comprises a pump housing 252 with first and second ends 286, 288, respectively, and a rotor 254 configured to be rotatably disposed within the housing 252. These components are configured in a particular manner relative to each other as follows.

Housing 252 includes an axial inlet at end 286 leading to central bore 258 configured for housing an impeller 256 of the rotor 254. The impeller 256 generally comprises a plurality of helical sweeping blades. Pump assembly 250 incorporates mixed-flow hydraulics having rotor blades only. While the specific configuration and relative arrangement of such impeller blades 256 shown in FIG. 11 is considered of beneficial use, other configurations may be employed as would be apparent to one of ordinary skill. In this configuration, the bore 258 has an increasing cross-section or diameter from end 286 toward the impeller blades 256. The combination of the central bore 258 and impeller 256 operate as a pumping chamber configured to draw blood flow $F_I$ into the central bore 258.

The housing 252 has a first section 280 starting at end 286 and extending axially toward, but short of, end 288 of the housing 252. First housing section 280 terminates distally at a larger diameter than the diameter of the remainder of the housing 252, such that the first section 280 forms an annular opening 260 in communication with and at the far end of central bore 258. Annular opening 260 forms an axially oriented outlet for an axial outlet flow $F_{OA}$ out of the cylindrical bore or pumping chamber 258. Furthermore, blood flow $F_{OR}$ is directed radially outward from the central bore 258 via a plurality of radial ports 272. The configuration of pump 250 is shown in FIG. 5 and FIG. 6 as having 3 radial ports 272 in housing 252. However, it is appreciated that any number of ports may be included.

Opposite from impeller 256, the rotor 254 comprises planar bearing surface 284 configured to mate with planar bearing surface 282 of the housing 252 via a journal bearing fit between the two surfaces to form a hydrodynamic journal bearing. The formed hydrodynamic bearing is a function of the spacing between the mating planar surfaces 282/284, which comprises a gap or leak path 274 for blood to lubricate and flow within the bearing.

During normal operation of the pump assembly 250 as shown in the operating configuration of FIG. 11, rotational motion of the rotor 254 within housing 252 is generally achieved via a magnetically-driven, sealed radial motor or actuator comprising a rotor stator 266 driving internal rotor 262 having one or more magnets 268 all disposed within sealed cavity 264. Motor stator 266 comprises an electrically conductive coil (not shown) that is adapted to be coupled to a power source (not shown) via leads. Motion of the internal rotor, and thus magnets 268, creates a rotating magnetic field coupling with corresponding magnets 270 in rotor 254, wherein the magnetic field extends across the clearance (i.e. leakage path 275) between the rotor 254 and housing 252 to displace the rotor magnets 270 sufficient to torque the rotor 254 and rotate the rotor 254.

Upon rotation of the rotor 254 within the pump housing 252, the impeller 256 draws blood flow $F_I$ inward from the axial inlet at end 286 and into the pumping chamber defined by central bore 258. Blood is directed into the axial port in-line with respect to the longitudinal or rotational axis of the rotor 254. The direction of the inlet flow of blood $F_I$ and outlet flow of blood $F_{OA}$ are primarily axial, while radial outlet flow $F_{OR}$ has at least a significant axial component. The axial port at end 286 may be coupled to a first end of cannula (not shown) with the pump 250 located at a first location of the circulatory system, wherein the output flow $F_O$ is dispersed into the first end of cannula for distributing the output flow of blood to a second end of the cannula at a second location in the circulatory system. It is also appreciated that the flow of blood as shown in FIG. 11 may be reversed (e.g. via reversing direction of impeller 256 or orientation of impeller blades) such that annular aperture 260 and ports 272 are inputs, and axial port at end 286 is an output.

Rotor 254 is supported first by the magnetic coupling across leak path 274, which results in a magnetic "pre-load" that the hydrodynamic bearing pushes against. The load on this flat thrust bearing varies as a function of rotor 254 speed (wherein the faster the rotor speed, the more the rotor 254 will want to move away from the magnetic coupling). However, axial translation of the rotor is limited by interaction and geometric constraints of impeller blades 256 and the shroud 280. The opposing surfaces may be optimized via material selection and geometric form to reduce mechanical wear. For example, one geometric form may be implemented as a taper (not shown) on the outer form of the blades 256 to induce a hydrodynamic bearing effect when in close proximity. The geometric and hydrodynamic interaction detailed above for pump assembly 250 may also be present or used for the pump assembly 100 and 150 of FIG. 5 and FIG. 7, where the axial preload is determined by a mixed axial/radial magnetic coupling.

Leakage flow within the leak path 274 is driven by geometry (i.e. pumping grooves) on the rotor 254 or housing 252. The direction of leak path flow can be reversed based on the rotor 254 geometry. All such tight clearance, low flow surfaces along leakage path 274 are continuously washed with motion, and hemolysis and thrombosis can be minimized as the active leakage flow path 274 through moving parts allows active washing of exposed surfaces.

In a preferred embodiment, the bearing surfaces comprise a flat hydrodynamic bearing within the leak path 274 through the motor, as provided in PCT international application number PCT/US16/30445, filed on May 2, 2016, to provide additional stability and flow characteristics to the rotor 254. A flat axial thrust bearing may be is disposed at flat end 282 of rotor 254. In one configuration, the axial thrust bearing comprises three longitudinally-oriented sweeping-tapered grooves that transverse toward the flat end 282. The thrust bearing is configured to provide a pressure differential and accordingly pumping mechanism to promote flow through leakage path 274. The flat bearing may also benefit from two bearing feature sets-one radial and one axial. In some embodiments, a thrust bearing design may include tapered-land grooves (not shown) in place of or in addition to longitudinal grooves.

A radial flange 276 may also be incorporated at end 286 to support coupling of a cannula (not shown) or other conduit.

A flexible cannula (not shown) may be attached to the pump body or housing of any of pumps 10, 50, 100, 150, 200 and 250. In such configuration, the pump would draw input flow $F_I$ of blood from within a first end of cannula, the second end of the cannula being positioned at a different location in the circulatory system.

It is to be appreciated that the various device/pump embodiments of the present disclosure significantly benefit objectives of minimally invasive and less invasive insertion methods are permitted by, as herein described and apparent to one of ordinary skill based upon a comprehensive review of the present disclosure. Two particularly beneficial methods for less invasive surgical implantation are disclosed, though without limitation, and which include: 1) insertion without vascular anastomosis, and 2) insertion with vascular anastomosis.

Minimally invasive insertion is considered of particular benefit to the extent that it allows the implementation of VADs (e.g. LV/LA, or RV/RA) without a thoracotomy or cardiopulmonary bypass. Central vascular access is considered of particular benefit to the extent that it is achieved via peripheral vascular access, such as for example using fluoroscopic guidance, for the placement of either an intravascular pump or specialized cannulas.

Less invasive insertion is considered of particular benefit to the extent that it includes placing the LVAD with a limited surgical incision and without cardiopulmonary bypass. Methods which eliminate the need for vascular anastomoses are furthermore considered very advantageous, and are beneficially achieved according to certain of the present embodiments. Adaptation to an insertion method facilitated by thorascopic techniques further simplifies the procedure, and is also achieved by certain of the present embodiments.

Minimally invasive placement of LVADS is generally considered to fall, predominately, within the domain of the interventional cardiologist (though clearly other adequately trained and capable physicians may practice the present disclosure). Adaptation for use by such interventionalist is provided by certain of the present embodiments, in particular in that such devices generally allow at least one of, and preferably more than one or all of: 1) a simple means for achieving non-thoracotomy vascular access, 2) small cannula systems and miniature pumps suitable for insertion in peripheral arteries, 3) small pumps suitable for subcutaneous implantation on the chest wall, and 4) pumps capable of operating reliably for months to years in an ambulatory setting. An ability to provide minimally or less invasive implantation of LVADs capable of operating reliably in extended ambulatory is a particular benefit presented by certain of the present embodiments and not previously possible by devices and methods of prior disclosures or use.

Various methods are made available by certain present embodiments and which are based on transvascular techniques familiar to the interventional cardiologist. Such methods typically employ placement of a flexible cannula retrograde across the aortic valve to serve as an inflow conduit to a pump. Non-thoracotomy placement of the inflow cannula will typically be via peripheral arterial access. One illustrative method employs placement of a miniature intravascular pump which receives power from an external controller and battery via a percutaneous wire.

For further illustration of one particular method, a pump system is employed that includes a miniaturized pump (e.g. any of pumps 10, 50, 100, 150, 200 and 250 illustrated in FIG. 1 through FIG. 12) that is placed within an artery of an arterial system. An inflow cannula is placed retrograde across an aortic valve into left ventricle of heart. The pump outlet is positioned in an ascending aorta of the arterial system. Blood is then removed from the left ventricle via the inflow cannula and pumped into the ascending aorta via the inlet port, thus, directly assisting the left ventricle.

Diastolic heart failure (DHF) may also be assisted by placing the pump inflow in the left atrium (LA) and sending blood to the aorta.

In all embodiments, power may be supplied to the pump 10, 50, 100, 150, 200 and 250 via a percutaneous wire (not shown) from an externally worn motor controller and rechargeable battery system (not shown). In one particular embodiment, the wire is coupled from the external system components to the pump via the subclavian artery. Alternatively, implantable battery and controller may be used, which is powered via transcutaneous electron transfer (TET).

In another embodiment, a system may incorporate the anatomical placement of a pump located in a subcutaneous pouch (not shown) in a pectoral region of a patient. The inflow of the pump is in continuity with a flexible inflow cannula (not shown) which enters the subclavian artery and traverses retrograde across the aortic valve into the left ventricle. A second outflow cannula connects to the outflow of the pump and returns blood to the arterial system—in this case, via an anastomosis at the contralateral subclavian artery. So configured, blood is removed from the left ventricle and returned to the systemic circulation, thus, directly assisting the left ventricle. As with the previously described system, a percutaneous wire may be used to supply power and/or control to the pump via an externally worn motor controller and rechargeable battery system.

In some embodiments, the pump system, implant configuration, and surgical methods may be conducted without requiring anastomosis of inflow or outflow cannulas to major vessel walls. It is also to be appreciated that these non-anastomotic methods could be adapted to a mini-thoracotomy or thorascopic approach without the need for cardiopulmonary bypass or anastomosis of a vascular graft.

In another embodiment, a pump system employs a pump (e.g. any of pumps 10, 50, 100, 150, 200 and 250 illustrated in FIG. 1 through FIG. 12) that is positioned in a left ventricle and with an outlet cannula that is passed antegrade through the aortic valve. This surgical procedure may be implemented via a small thoracotomy. According to such a method, the pericardium is opened and traction is placed on the ventricular apex. Using puncture techniques and a dilator system, a thin walled trochar is then advanced into the ventricular cavity. The pump, such as a forward flow pump, is then advanced into the left ventricle and the flexible outflow cannula (not shown) is readily advanced antegrade across the aortic valve. The pump is then anchored at the ventricular apex using an anchor assembly, which may be chosen of suitable construction and operation in context with the system and methods described as apparent to one of ordinary skill.

In such configuration, the pump draws blood through ports (e.g. axial inlet port in any of pumps 10, 50, 100, 150, 200 and 250) in the housing, and pumps the blood forward through the outlet cannula into the supravalvular aorta. The aortic leaflets would generally provide sufficient seal around the outlet cannula.

According to further aspects of a pump system consistent with certain embodiments herein described, less invasive surgical insertion with a vascular anastomosis is performed via a small thoracotomy without cardiopulmonary bypass. Though not herein shown, for further illustration such method may proceed for example as follows.

The pericardium is opened and traction applied to the ventricular apex. Using puncture techniques and a dilator system, a thin walled inflow cannula is inserted into the left ventricle. The outflow graft may be anastomosed to the descending thoracic aorta. Alternatively, the outflow graft could be tunneled to the subclavian or femoral artery for anastomosis. A pump is then placed between the inflow and outflow grafts such that blood is removed from the left ventricle and pumped into the systemic circulation. The pump may be implanted in the thoracic cavity, or subcutaneously, or elsewhere as may be appropriate in a particular case or technique. A percutaneous wire provides power to the pump via an external controller and battery system.

Current left ventricular assist devices generally require surgical cannulation of the left ventricle via the ventricular apex and surgical anastomosis of an arterial graft to the thoracic aorta. The vast majority are too large for placement in the pericardial space or thoracic cavity and are implanted below the diaphragm in the anterior abdomen region. Subdiaphragmatic placement typically requires tunneling through the diaphragm to route the vascular grafts—this is a big operation and usually requires cardiopulmonary bypass. Placement of the pump in the pericardial space eliminates the need for diaphragmatic penetrations and minimizes the length of the pump inlet. A short pump inlet may reduce the likelihood of thrombus formation in the pump by reducing the amount of work required for pumping.

Various LVAD pump embodiments of the present disclosure are described more fully below. Each is considered to offer certain significant potential advantages over previously disclosed or used systems. Such improvements of the certain embodiments include, without limitation, one or more of the following: simplicity of design, reduction in cost, and reduction of power consumption over existing LVAD designs, and each could readily be adapted to conventional surgical insertion. Moreover, certain embodiments are considered to present the highly beneficial advantage of combining low profile, minimally invasive or less invasive delivery, with longevity of life as extended ambulatory implants.

In addition, the outer diameter and length of the pumps described herein may be readily adjusted to suit an appropriate parameter for a particular application to optimize motor performance and hydrodynamic bearing support for radial constraint of the rotating assembly.

Among other benefits, the pumps of the present description allow for a size envelope that is well suited for insertion into the left ventricular apex or atrium via a mini-thoracotomy and would occupy very little extra-cardiac volume. A vascular graft from the pump outlet would typically be anastomosed to an aorta or a subclavian artery.

The pumps according to the present description may also be constructed small enough that it could be located on the anterior chest wall and receive blood from a transthoracic cannula to the left heart and return flow to the circulation via a graft to the subclavian artery. Access to the left ventricle could also be achieved with a thin-walled cannula placed via the subclavian artery, retrograde across the aortic valve. The aortic valve leaflets would seal around the wall of the cannula. Pressurized flow from the pump outlet could be returned to the circulation via a graft to a peripheral artery such as the subclavian. Such a procedure would be in the domain of the interventional cardiologist.

In one particular further embodiment of use, a pump as detailed in the present description may be inserted into the left ventricular apex or atrium via a mini-thoracotomy, and would occupy very little extra-cardiac volume. A vascular graft from the pump outlet could be anastomosed to the aorta or the subclavian artery. The pump is also small enough that it could be located on the anterior chest wall and receive blood from a transthoracic cannula to the left heart and return flow to the circulation via a graft to the subclavian artery. Likewise, access to the left heart could be achieved with a thin-walled cannula placed via the subclavian artery, retrograde across the aortic valve left and flow returned to the circulation via a graft to the subclavian artery.

The combination of features of the pumps of the present description are generally suited for direct placement in the left ventricle or atria, though radially enlarged features if appropriately constructed or otherwise modified to be collapsed during delivery may allow for more reduced profiles for minimally or less invasive delivery.

In another exemplary embodiment, a proximal end of a cannula (not shown) is coupled to the input end (e.g. port 24 of any of pumps 10a through 10e) of the pump, with the distal end inserted through a small hole in the ventricular apex and the outflow cannula passed antegrade across the aortic valve such that the tip of the cannula was above the aortic valve. The aortic valve leaflets would seal around the cannula wall. The outflow cannula could be reinforced or, possibly an inflatable pantaloon design to minimize abrasion of the valve leaflets. The cannula diameter could be much smaller than the pump body. The outer diameter of the outflow cannula as it traverses the aortic valve could be for example approximately 7 mm. The main body of the pump with the pump inlet would remain in the left ventricle.

During pump operation blood would be pump from the left ventricle into the supravalvular aorta.

While this disclosure has been described in conjunction with the specific embodiments outlined above, it is evident that many alternatives, modifications and variations will be apparent to those skilled in the art. For example, whereas present embodiments may be described by reference to conductor wires connecting pump motors to external power sources, other power sources or energy coupling mechanisms may be used, such as integral batteries, implanted power sources. Such may further include, for example, implanted batteries that are either integral with the pump assembly or remotely implanted. In various locations, suitable batteries may furthermore have for example fixed charge life, or may be rechargeable, such as via motion actuation or via transcutaneous inductive coupling. According to another example, certain mating or cooperating parts such as rotor magnets and motor stator backirons are shown in specific relative locations to each other according to the specific illustrative embodiments. However, other specific arrangements relative between such components are also contemplated and may also be suitable or even of particular benefit in certain circumstances or applications. For example, whereas the back iron of motor stator embodiments shown is typically shown aligned with the rotor magnet, it may instead be partially longitudinally displaced from the rotor magnet in resting condition. This resting displacement may be configured in order to maximize the displacement force from the magnetic attraction between these components counter-directionally against opposite longitudinal displacement forces incurred by the rotor within the housing when the magnetic flux gap motor is activated.

Furthermore, it is appreciated that features or components of any of the embodiments described herein may be interchangeably used where appropriate.

From the description herein, it will be appreciated that the present disclosure encompasses multiple embodiments which include, but are not limited to, the following:

1. A heart assist device, comprising: a rotor; said rotor comprising a shaft with an outer surface and an impeller extending from the shaft at a first location on the outer surface; said outer surface comprising an outer bearing surface at a second location on the shaft; a pump housing comprising a first end and a second end; the pump housing comprising one or more cylindrical bores configured to define a pumping chamber and an inner bearing surface within the pump housing; wherein, in an operating configuration, the rotor is positioned within the one or more cylindrical bores such that the impeller rotates within the pumping chamber upon actuation of the rotor; wherein said inner bearing surface of the pump housing is closely fitted to said outer bearing surface of said shaft to form a hydrodynamic bearing clearance there between such that during actuation of the rotor the inner bearing surface and outer bearing surface form a hydrodynamic journal bearing; the pump housing comprising an axial inlet at the first end of the pump housing, the axial inlet in fluid communication with the pumping chamber; the pump housing further comprising an annular outlet in communication with the pumping chamber, the annular outlet being located between the first and second ends of the pump housing; wherein the pump housing comprises a leakage outlet in fluid communication with the hydrodynamic bearing clearance; wherein actuation of the rotor causes blood to enter into the axial inlet, through the pumping chamber, and out the annular outlet in a substantially axial outlet flow; and wherein during actuation of the rotor the hydrodynamic bearing clearance operates as a leakage path to allow the flow of blood into a leakage inlet, and along the length of the hydrodynamic bearing clearance.

2. The device or pump of any of the preceding or following embodiments, wherein said rotor is primarily suspended in the radial direction within said housing by hydrodynamic thrust forces generated by relative movement of said rotor with respect to and within said pump housing.

3. The device or pump of any of the preceding or following embodiments: wherein said rotor comprises one or more rotor magnets located within the bearing surface of said shaft; wherein the pump housing comprises a motor stator having a coil positioned opposite said one or more rotor magnets from the hydrodynamic bearing clearance; and wherein actuation of the rotor is affected by electrical current flowing through the motor stator to generate magnetic flux field that extends across the leakage flow path to displace the one or more rotor magnets.

4. The device or pump of any of the preceding or following embodiments: wherein the one or more cylindrical bores comprises a first bore disposed at the first end of the pump housing, the first bore configured for housing the impeller and pumping chamber, and a second bore at a second end of the pump housing, the second bore defining the inner bearing surface configured for housing the outer bearing surface of the rotor and leakage flow path; wherein rotation of the impeller draws the flow of blood through the axial inlet port and a first portion into the pumping chamber, and into the leakage flow path; wherein the first portion of the blood is directed along the length of the second bore and through an outlet disposed toward the second end of the pump housing; and wherein a second portion of blood is directed out the annular outlet.

5. The device or pump of any of the preceding or following embodiments, the pump housing further comprising: one or more radial outlet ports disposed along a circumference of the pump housing at a location between the first end and the annular outlet, wherein a third portion of blood is directed radially outward from the one or more radial outlet ports.

6. The device or pump of any of the preceding or following embodiments wherein the motor stator one and one or more rotor magnets are axially disposed with respect to each other to form an axial motor.

7. The device or pump of any of the preceding or following embodiments, wherein the hydrodynamic bearing clearance comprises an annular gap formed between the inner bearing surface of the pump and said outer bearing surface of said shaft.

8. The device or pump of any of the preceding or following embodiments, wherein the hydrodynamic bearing clearance further comprises a conical leakage path in fluid communication with the annular gap, the conical leakage path formed from a conical bearing interface between the rotor and pump housing.

9. The device or pump of any of the preceding or following embodiments, wherein the conical leakage path is located upstream from the annular gap between the pumping chamber and annular gap.

10. The device or pump of any of the preceding or following embodiments, wherein the conical leakage path is located downstream from the annular gap opposite the pumping chamber from the annular gap.

11. The device or pump of any of the preceding or following embodiments: wherein the hydrodynamic bearing clearance further comprises a second conical leakage path in fluid communication with the annular gap; wherein the second conical leakage path is formed from a second conical bearing interface between the rotor and pump housing; and wherein the second conical leakage path is located downstream from the annular gap.

12. The device or pump of any of the preceding or following embodiments, wherein the hydrodynamic bearing clearance further comprises a spherical leakage path in fluid communication with the annular gap, the spherical leakage path formed from a spherical bearing interface between the rotor and pump housing.

13. The device or pump of any of the preceding or following embodiments: wherein the leakage path is formed between a conical bearing interface between the rotor and pump housing; and wherein the motor stator one and one or more rotor magnets are disposed across the conical bearing interface from one another.

14. A pump for providing circulatory assistance within the circulatory system of a patient, comprising: a rotor comprising a shaft with an outer surface and an impeller extending from the shaft at a first location on the outer surface; said outer surface comprising an outer bearing surface at a second location on the shaft; a pump housing comprising a first end and a second end; the pump housing comprising one or more cylindrical bores configured to define a pumping chamber and an inner bearing surface within the pump housing; wherein, in an operating configuration, the rotor is positioned within the one or more cylindrical bores such that the impeller rotates within the pumping chamber upon actuation of the rotor; wherein said inner bearing surface of the pump housing is closely fitted to said outer bearing surface of said shaft to form a hydrodynamic bearing clearance there between such that during actuation of the rotor the inner bearing surface and outer bearing surface form a hydrodynamic journal bearing; the pump housing comprising an axial inlet at the first end of the pump housing, the axial inlet in fluid communication with a first location in the circulatory system and the pumping chamber; the pump housing further comprising an annular outlet in communication with the pumping chamber, the annular outlet being located between the first and second ends of the pump housing; wherein actuation of the rotor causes blood from the first location in the circulatory system to enter into the axial inlet, through the pumping chamber, and exit out the annular outlet to a second location in the circulatory system; and wherein during actuation of the rotor the hydrodynamic bearing clearance operates as a leakage path to allow the flow of blood into a leakage inlet, and along the length of the hydrodynamic bearing clearance.

15. The device or pump of any of the preceding or following embodiments, wherein the pump housing comprises a leakage outlet in fluid communication with the hydrodynamic bearing clearance, the leakage outlet directing the blood out the leakage path to a third location in the circulatory system.

16. The device or pump of any of the preceding or following embodiments, wherein the blood exits out the annular outlet in a substantially axial outlet flow.

17. The device or pump of any of the preceding or following embodiments, wherein the one or more cylindrical bores comprises a first bore disposed at the first end of the pump housing, the first bore configured for housing the impeller and pumping chamber, and a second bore at a second end of the pump housing, the second bore defining the inner bearing surface configured for housing the outer bearing surface of the rotor and leakage flow path; wherein rotation of the impeller draws the flow of blood through the axial inlet port and a first portion into the pumping chamber, and into the leakage flow path; wherein the first portion of the blood is directed along the length of the second bore and through the leakage outlet disposed toward the second end of the pump housing; and wherein a second portion of blood is directed out the annular outlet.

18. The device or pump of any of the preceding or following embodiments, the pump housing further comprising: one or more radial outlet ports disposed along a circumference of the pump housing at a location between the first end and the annular outlet; wherein a third portion of blood is directed radially outward from the one or more radial outlet ports.

19. The device or pump of any of the preceding or following embodiments, wherein the hydrodynamic bearing clearance comprises an annular gap formed between the inner bearing surface of the pump and said outer bearing surface of said shaft.

20. The device or pump of any of the preceding or following embodiments, wherein the hydrodynamic bearing clearance further comprises a conical leakage path in fluid communication with the annular gap, the conical leakage path formed from a conical bearing interface between the rotor and pump housing.

21. The device or pump of any of the preceding or following embodiments, wherein the conical leakage path is located upstream from the annular gap between the pumping chamber and annular gap.

22. The device or pump of any of the preceding or following embodiments, wherein the conical leakage path is located downstream from the annular gap opposite the pumping chamber from the annular gap.

23. The device or pump of any of the preceding or following embodiments: wherein the hydrodynamic bearing clearance further comprises a second conical leakage path in fluid communication with the annular gap; wherein the second conical leakage path is formed from a second conical bearing interface between the rotor and pump housing; and wherein the second conical leakage path is located downstream from the annular gap.

24. A heart assist device, comprising: a rotor comprising a shaft and an impeller extending from the shaft at a first location on the shaft; said rotor comprising a rotor bearing surface at a second location on the shaft; a pump housing comprising a first end and a second end; the pump housing comprising one or more cylindrical bores configured to define a pumping chamber and an inner bearing surface within the pump housing; wherein, in an operating configuration, the rotor is positioned within the one or more cylindrical bores such that the impeller rotates within the pumping chamber upon actuation of the rotor; wherein said inner bearing surface of the pump housing is closely fitted to rotor bearing surface to form a hydrodynamic bearing clearance there between such that during actuation of the rotor the inner bearing surface and rotor bearing surface form a hydrodynamic journal bearing; the pump housing comprising an axial inlet at the first end of the pump housing, the axial inlet in fluid communication with the pumping chamber; the pump housing further comprising an annular outlet in communication with the pumping chamber, the annular outlet being located between the first and second ends of the pump housing; wherein actuation of the rotor causes blood to enter into the axial inlet, through the pumping chamber, and out the annular outlet in a substantially axial outlet flow; and wherein during actuation of the rotor the hydrodynamic bearing clearance operates as a leakage path to allow the flow of blood into a leakage inlet, and along the length of the hydrodynamic bearing clearance.

25. The device or pump of any of the preceding or following embodiments, wherein said rotor comprises one or more rotor magnets located within the bearing surface of said shaft; wherein the pump housing comprises a motor stator having a coil positioned opposite said one or more rotor magnets from the hydrodynamic bearing clearance; and wherein actuation of the rotor is affected by electrical current flowing through the motor stator to generate magnetic flux field that extends across the leakage flow path to displace the one or more rotor magnets.

26. The device or pump of any of the preceding or following embodiments, wherein the motor stator one and one or more rotor magnets are axially disposed with respect to each other to form an axial motor.

27. The device or pump of any of the preceding or following embodiments, wherein the hydrodynamic bearing clearance comprises an annular gap formed between the inner bearing surface of the pump and said outer bearing surface of said shaft.

28. The device or pump of any of the preceding or following embodiments, wherein the hydrodynamic bearing clearance further comprises a conical leakage path in fluid communication with the annular gap, the conical leakage path formed from a conical bearing interface between the rotor and pump housing.

29. The device or pump of any of the preceding or following embodiments, wherein the hydrodynamic bearing clearance further comprises the spherical leakage path formed from a spherical bearing interface between the rotor and pump housing.

30. The device or pump of any of the preceding or following embodiments, wherein the inner bearing path and rotor bearing path comprise planar surface forming a planar hydrodynamic bearing and planar leakage path in fluid communication with the pumping chamber.

As used herein, the singular terms "a," "an," and "the" may include plural referents unless the context clearly dictates otherwise. Reference to an object in the singular is not intended to mean "one and only one" unless explicitly so stated, but rather "one or more."

As used herein, the term "set" refers to a collection of one or more objects. Thus, for example, a set of objects can include a single object or multiple objects.

As used herein, the terms "substantially" and "about" are used to describe and account for small variations. When used in conjunction with an event or circumstance, the terms can refer to instances in which the event or circumstance occurs precisely as well as instances in which the event or circumstance occurs to a close approximation. When used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, "substantially" aligned can refer to a range of angular variation of less than or equal to ±10°, such as less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°.

Additionally, amounts, ratios, and other numerical values may sometimes be presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

All structural and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A heart assist device, comprising:
   (a) a rotor comprising a shaft and an impeller extending from the shaft at a first location on the shaft;
   (b) said rotor comprising a rotor bearing surface at a second location on the shaft as a bearing interfacing with a thrust bearing, forming a bearing interface which is hemispherical or conical and provides a pressure differential as a pumping mechanism to promote flow through a leakage path of the bearing interface;
   (c) wherein said rotor is configured with a rotor magnet for being magnetically driven by a motor stator;
   (d) wherein said first location and said second location on said rotor are toward opposite ends of said rotor;
   (e) a pump housing comprising a first end and a second end;
   (f) wherein the pump housing comprises one or more cylindrical bores configured to define a pumping chamber and an inner bearing surface within the pump housing;
   (g) wherein, in an operating configuration, the rotor is positioned within the one or more cylindrical bores whereby the impeller rotates within the pumping chamber upon actuation of the rotor;

(h) wherein said inner bearing surface of the pump housing is sufficiently closely fitted to said rotor to form a hydrodynamic bearing clearance there between whereby during actuation of the rotor the one or more cylindrical bores and an outer bearing surface of the shaft form a hydrodynamic journal bearing;

(i) wherein said hydrodynamic bearing clearance comprises an annular gap formed between the inner bearing surface of the pump housing and said outer bearing surface of said shaft;

(j) the pump housing comprising an axial inlet at the first end of the pump housing, with the axial inlet in fluid communication with the pumping chamber, with an annular outlet located circumferentially in a middle region of the pump housing between said first and second ends of the pump housing; and (k) wherein actuation of the rotor causes blood to enter into the axial inlet, through the pumping chamber, and then out of the device through both the annular outlet on the circumference of the device in a substantially axial outlet flow and a separate leakage outlet connecting to the leakage path at the bearing, wherein a radial port on a side of the pump housing defines the separate leakage outlet.

2. The device of claim 1, wherein said pump housing comprises a first housing section which contains the pumping chamber toward said first end of said pump housing, and which overlaps a second housing section which has a smaller diameter than said first housing section, and which is toward said second end of said pump housing, so that said annular outlet is disposed circumferentially between an overlap of an interior of said first housing section over an exterior of said second housing section.

3. The device of claim 1, wherein during actuation of the rotor, the hydrodynamic bearing clearance operates as part of the leakage path to allow the flow of blood into a leakage inlet, and along the length of the hydrodynamic bearing clearance.

4. The device of claim 1, wherein the hydrodynamic bearing clearance further comprises part of the leakage path between the rotor and pump housing;

wherein hydrodynamic thrust forces generated by the relative motion of the rotor with respect to the inner bearing surface provide for radial suspension of the rotor within the cylindrical bore; and wherein said hydrodynamic bearing clearance encompasses said bearing interface between said bearing at the end of said rotor which is opposite from said impeller, and the pump housing forming said leakage path in fluid communication with the annular gap.

5. The device of claim 1, wherein the motor stator is axially offset with respect to the rotor magnet to form an axial force preloading the shaft of the rotor into the one or more cylindrical bores of the pump housing in which the shaft is disposed.

6. The device of claim 1, wherein the bearing interface which provides the pressure differential as the pumping mechanism to promote flow through the leakage path of the bearing interface includes grooves on the rotor.

* * * * *